US009383435B2

(12) United States Patent
Osawa

(10) Patent No.: US 9,383,435 B2
(45) Date of Patent: Jul. 5, 2016

(54) ULTRASOUND PROBE

(75) Inventor: Atsushi Osawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 7 days.

(21) Appl. No.: 13/302,127

(22) Filed: Nov. 22, 2011

(65) Prior Publication Data

US 2012/0150038 A1 Jun. 14, 2012

(30) Foreign Application Priority Data

Dec. 8, 2010 (JP) ................................. 2010-273660

(51) Int. Cl.
*A61B 8/00* (2006.01)
*G01S 7/52* (2006.01)
*G01S 7/00* (2006.01)

(52) U.S. Cl.
CPC ............. *G01S 7/5208* (2013.01); *A61B 8/4444* (2013.01); *A61B 8/56* (2013.01); *A61B 8/44* (2013.01); *A61B 8/4472* (2013.01); *G01S 7/003* (2013.01)

(58) Field of Classification Search
USPC .................................................. 600/437, 443
See application file for complete search history.

(56) References Cited

U.S. PATENT DOCUMENTS

| 4,413,629 | A | * | 11/1983 | Durley, III | ..................... 600/453 |
| 5,961,465 | A | * | 10/1999 | Kelly et al. | ..................... 600/459 |
| 7,348,713 | B2 | | 3/2008 | Hashimoto | |
| 2003/0195418 | A1 | * | 10/2003 | Barnes et al. | ................. 600/437 |
| 2008/0146924 | A1 | * | 6/2008 | Smith et al. | .................... 600/437 |
| 2010/0160785 | A1 | * | 6/2010 | Poland et al. | .................. 600/459 |
| 2012/0143060 | A1 | * | 6/2012 | Weekamp et al. | ............. 600/459 |

FOREIGN PATENT DOCUMENTS

| JP | 04-250145 | 9/1992 |
| JP | 2001-74710 | 3/2001 |
| JP | 2006-25892 | 2/2006 |
| JP | 2006-102135 | 4/2006 |
| JP | 2007-209699 | 8/2007 |
| JP | 2009-261840 | 11/2009 |
| JP | 2009-297352 | 12/2009 |
| JP | 2010-528698 | 8/2010 |

OTHER PUBLICATIONS

Official Action issued Dec. 4, 2012 by the Japanese Patent Office in Japanese Patent Application No. 2010-273660 with partial English translation, 4 pages.
Notification of Reasons for Refusal issued Sep. 18, 2012 by Japanese Patent Office in corresponding Japanese Patent Application No. 2010-273660 with Partial English translation, 6 pages.

(Continued)

*Primary Examiner* — Long V Le
*Assistant Examiner* — Ellsworth Weatherby
(74) *Attorney, Agent, or Firm* — Young & Thompson

(57) ABSTRACT

An ultrasound probe which transmits ultrasonic waves to a subject, receives ultrasonic echoes generated by reflection of the ultrasonic waves on the subject and outputs ultrasound image signals includes a case having a grip portion set therein and functional units disposed in the case. The functional units include an ultrasonic wave-generating unit, at least one integrated circuit board and a battery. The battery disposed in the case at a position corresponding to the grip portion ensures the safety of operators from heat generated in the at least one integrated circuit board and the like.

7 Claims, 3 Drawing Sheets

(56) References Cited

OTHER PUBLICATIONS

Chinese Office Action dated Apr. 17, 2014; Patent Application No. 201110402453.3.

Chinese Office Action, dated Oct. 20, 2014, in corresponding Chinese Patent Application No. 201110402453.3, with partial English translation.

* cited by examiner

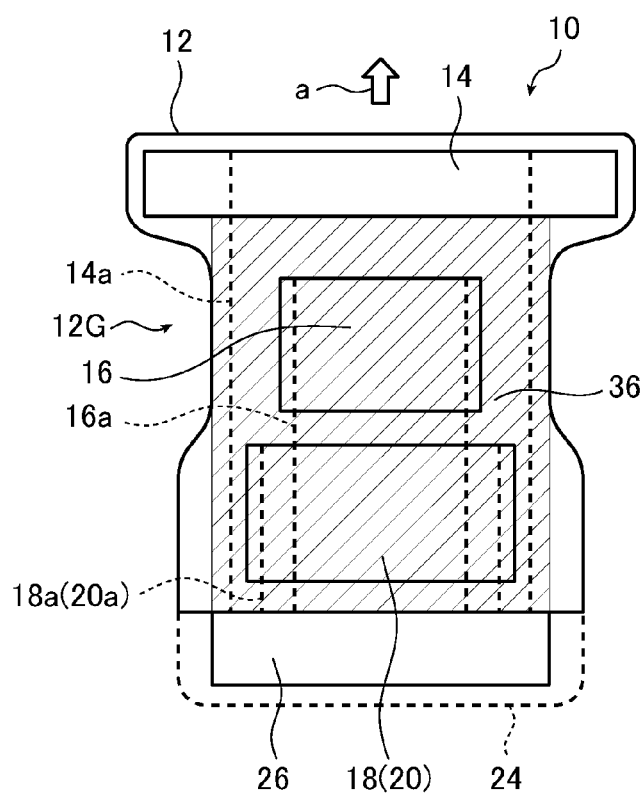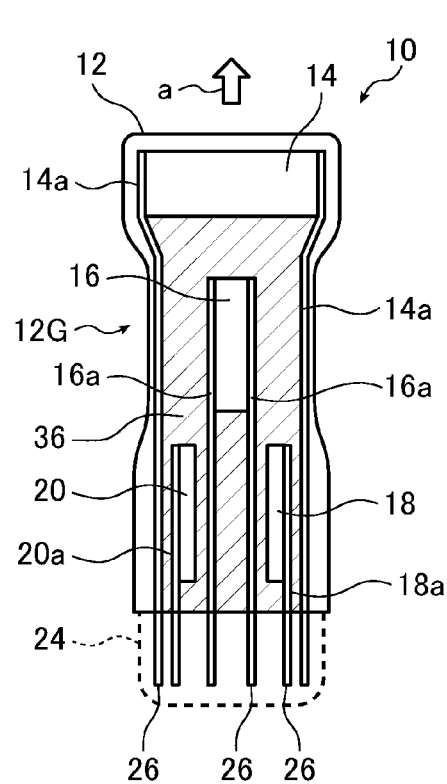

ULTRASOUND PROBE

BACKGROUND OF THE INVENTION

The present invention belongs to the technical field of ultrasound probes that may be used in ultrasound diagnostic apparatuses. The invention more specifically relates to an ultrasound probe which can provide operators with enhanced safety from heat.

Ultrasound diagnostic apparatuses using ultrasound images are put to practical use in the medical field.

In general, this type of ultrasound diagnostic apparatus includes an ultrasound probe (hereinafter referred to as "probe") and a diagnostic apparatus body. The probe transmits ultrasonic waves toward a subject and receives ultrasonic echoes from the subject, and the diagnostic apparatus body electrically processes reception signals to generate an ultrasound image.

The probe making up a part of such an ultrasound diagnostic apparatus has an ultrasonic wave-generating unit which transmits ultrasonic waves to a subject, receives ultrasonic echoes from the subject and outputs the received ultrasonic echoes as electric signals.

In addition to the ultrasonic wave-generating unit, the probe may also include integrated circuit boards for performing amplification and A/D conversion of signals outputted from the ultrasonic wave-generating unit and for changing the timing of transmission and reception of ultrasonic waves in the ultrasonic wave-generating unit.

The ultrasonic wave-generating unit transmits and receives ultrasonic waves to generate heat. A higher-definition ultrasound image is obtained with increasing power of ultrasonic waves transmitted from the ultrasonic wave-generating unit but the ultrasonic wave-generating unit generates more heat.

A diagnosis is usually made by bringing an acoustic lens of the ultrasonic wave-generating unit in the probe into contact with a subject. Therefore, the subject may be exposed to risk from heat if the temperature of the ultrasonic wave-generating unit increased too much.

Actuation of the integrated circuit board also causes heat generation. Therefore, in the probe having the integrated circuit board, heat generated in the integrated circuit board is transmitted to the ultrasonic wave-generating unit to increase its temperature.

Therefore, various proposals have been made to release heat in the ultrasonic wave-generating unit and the integrated circuit board from the probe to the outside thereby suppressing the heating of the ultrasonic wave-generating unit, ensuring the safety of subjects from heat and enabling diagnosis with high-power ultrasonic waves.

For example, JP 4-250145 A describes a probe (ultrasound probe) in which a joint portion is provided between a probe head portion having an ultrasonic wave-generating unit and a grip portion having an integrated circuit board, the cross-sectional area of the joint portion is made smaller than that of the probe head portion and the grip portion, and the joint portion is provided with radiator fins.

JP 2007-209699 A describes a probe including a first cooling means for cooling an ultrasonic wave-generating unit and a second cooling means for cooling an integrated circuit board.

Cooling means including a heat transfer means for transferring heat in the ultrasonic wave-generating unit and the integrated circuit board to the opposite end of the probe (rear end in the direction of transmission of ultrasonic waves) and a means for releasing the heat transferred by the heat transfer means may be used for the first and second cooling means.

JP 2009-261840 A describes a probe which includes a first heat release means for releasing to the outside of the probe in the lateral direction, heat in an ultrasonic wave-generating unit having a higher thermal resistance in the longitudinal direction in which ultrasonic waves are transmitted than in the lateral direction, and a second heat release means for conducting heat in an integrated circuit board laterally or backward in the direction of transmission of ultrasonic waves and releasing the conducted heat to the outside of the probe.

SUMMARY OF THE INVENTION

Such a probe having an ultrasonic wave-generating unit and an integrated circuit board can release heat of the ultrasonic wave-generating unit while preventing heat in the integrated circuit board from being transferred to the ultrasonic wave-generating unit.

As a result, it is possible to ensure the safety of subjects from heat generated in the probe and make safe ultrasound diagnoses while increasing the power of ultrasonic waves transmitted from the ultrasonic wave-generating unit.

Conventional probes give weight to the safety of subjects from heat but the safety of operators manipulating probes for ultrasound diagnoses (doctors making ultrasound diagnoses) is not taken into account at all.

An object of the present invention is to solve the foregoing prior art problems and to provide an ultrasound probe which includes not only an ultrasonic wave-generating unit and integrated circuit boards but also a battery for use as a power supply for driving the ultrasound probe and which ensures the safety of operators manipulating the ultrasound probe from heat.

In order to achieve the above object, the present invention provides an ultrasound probe comprising: a case having a grip portion set therein; and functional units disposed in said case and including at least an ultrasonic wave-generating unit which transmits ultrasonic waves to a subject, receives ultrasonic echoes generated by reflection of the ultrasonic waves on the subject and outputs signals in accordance with the received ultrasonic echoes, at least one integrated circuit board, and a battery disposed in said case at a position corresponding to said grip portion.

In the ultrasound probe of the invention, at least two of the functional units preferably include thermally conductive members for heat release independently of each other.

At least two of the functional units are preferably insulated from each other.

The thermally conductive members are preferably insulated from each other.

The thermally conductive members preferably have thermal conductivity which differs between a predetermined two-dimensional direction and a direction perpendicular to the two-dimensional direction, and the thermal conductivity is preferably higher in the predetermined two-dimensional direction than in the direction perpendicular to the two-dimensional direction.

One of the at least one integrated circuit board preferably has a function of performing wireless communication with a diagnostic apparatus body constituting an ultrasound diagnostic apparatus.

The ultrasound probe of the invention includes not only the ultrasonic wave-generating unit and the integrated circuit boards but also the battery for use in supplying electric power for driving the ultrasound probe. This battery is disposed at the position which corresponds to the grip portion for an operator (doctor making an ultrasound diagnosis) to hold and which is set in the case constituting the appearance of the ultrasound probe.

The amount of heat generation (heat release) during the use of the ultrasound probe having the integrated circuit boards and the battery is large in the integrated circuit boards but small in the battery. Accordingly, the inventive ultrasound probe having the foregoing configuration can suppress the heat generation in the grip portion held by an operator manipulating the ultrasound probe while appropriately ensuring the safety of the operator from heat.

BRIEF DESCRIPTION OF THE DRAWINGS

FIG. 1A is a side view conceptually showing an embodiment of an ultrasound probe of the invention and FIG. 1B is a plan view of the ultrasound probe shown in FIG. 1A.

DETAILED DESCRIPTION OF THE INVENTION

Figure 2A:
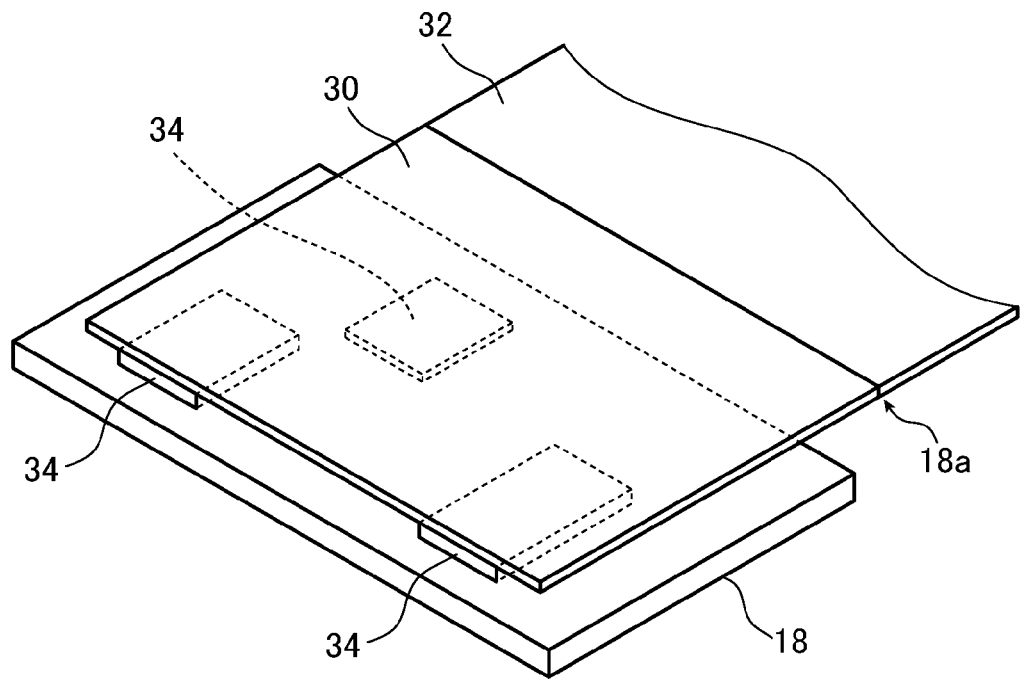
FIGS. 2A and 2B each conceptually show a method of disposing a thermally conductive member in the ultrasound probe shown in FIGS. 1A and 1B.

Next, the ultrasound probe of the invention is described in detail by referring to the preferred embodiments shown in the accompanying drawings.

FIGS. 1A and 1B conceptually show the configuration of an ultrasound probe of the invention.

FIG. 1A is a side view and FIG. 1B is a plan view. Ultrasound transducers 46 of an ultrasonic wave-generating unit 14 to be described later are disposed transversely in FIG. 1A and in a direction perpendicular to the plane of paper in FIG. 1B.

An ultrasound probe 10 (hereinafter referred to as "probe 10") shown in FIGS. 1A and 1B is a wireless communication type ultrasound probe which transmits ultrasonic waves to a subject, receives ultrasonic echoes from the subject, converts the received ultrasonic echoes into electric signals, processes the electric signals and transmits the processed electric signals as ultrasound image signals to a diagnostic apparatus body 42 to be described later through wireless communication.

The probe 10 basically includes a case 12, the ultrasonic wave-generating unit 14, a battery 16, a control board 18, a communication board 20, a cover 24 (shown by dotted lines in FIGS. 1A and 1B) and radiator fins 26.

The case 12 and the cover 24 constitute the appearance of the probe 10.

The case 12 accommodates therein the ultrasonic wave-generating unit 14, the battery 16, and the control board 18 and the communication board 20 each serving as an integrated circuit board. Although not shown, these components in the case 12 are appropriately connected to each other by power lines and electric signal lines.

The radiator fins 26 for releasing heat in functional units such as the ultrasonic wave-generating unit 14 disposed in the case 12 to the outside are provided at the rear end of the case 12 (at the rear end in the direction of transmission of ultrasonic waves shown by arrow "a" in FIGS. 1A and 1B). The radiator fins 26 are not particularly limited and various known radiator fins (radiation means) such as plates made of metals with high thermal conductivity (e.g., aluminum and copper) can be used.

The cover 24 is a member which is fixed to the rear end of the case 12 and covers the radiator fins 26. The cover 24 is formed from, for example, a mesh material, a punched metal or a plate having many slits so that the internal heat may be easily released.

As shown in FIGS. 1A and 1B, the case 12 of the probe 10 is narrowed on the rear side of the ultrasonic wave-generating unit 14 in the direction of transmission of ultrasonic waves. In the illustrated probe 10, this narrow position is set as a grip portion (holding portion) 12G for an operator (a doctor making an ultrasound diagnosis) to hold and manipulate the probe 10.

The battery 16 is disposed within the case 12 of the probe 10 of the invention at the position corresponding to the grip portion 12G.

The ultrasonic wave-generating unit 14, the battery 16, the control board 18 and the communication board 20 are functional units in the invention.

In the practice of the invention, the functional units are not limited to the ultrasonic wave-generating unit, the battery and the integrated circuit boards. In other words, in this invention, the functional units are disposed within the case constituting the appearance of the ultrasound probe and show an integral structural unit having an electric action. The functional units are optionally connected to each other by cables or FPC.

The ultrasonic wave-generating unit 14 (hereinafter referred to as "ultrasonic wave unit 14") is of a known type used in an ultrasound probe which transmits ultrasonic waves to a subject, receives ultrasonic echoes from the subject and outputs the received echoes as electric signals.

Therefore, known ultrasonic wave-generating units (acoustic units/piezoelectric oscillator units) for use in ultrasound probes may be used for the ultrasonic wave unit 14, as exemplified by an ultrasonic wave-generating unit obtained by covering a one-dimensional or two-dimensional array of ultrasound transducers 46 (see FIG. 3) with an acoustic lens, each of the ultrasound transducers including an ultrasound oscillator which has a piezoelectric body made of PZT (lead zirconate titanate) or PVDF (polyvinylidene fluoride) and an electrode formed at each end of the piezoelectric body, an acoustic matching layer, a backing layer and the like.

In the practice of the invention, there is no particular limitation on the type of the probe 10 and various types such as convex type, linear type and sector type can be used. The probe may be an external probe or a radial scan type probe for use in an ultrasonic endoscope.

In addition, the probe 10 of the invention may have an ultrasound oscillator compatible with harmonic imaging for use in receiving second or higher order harmonics from transmitted ultrasonic waves.

The probe 10 is wirelessly connected to the diagnostic apparatus body 42 to be described later and has no driving power line or electric signal line for external connection. The battery 16 supplies the respective components of the probe 10 with driving power.

The battery 16 is a known rechargeable battery and is recharged if necessary when held or put in a probe holder 96 of the diagnostic apparatus body 42.

The control board 18 is an integrated circuit board (electronic board) on which integrated circuits for controlling the probe 10, performing the transmission/reception of ultrasonic waves from/in the ultrasonic wave unit 14 and processing the signals received in the ultrasonic wave unit 14 is mounted. The communication board 20 is an integrated circuit board on which an integrated circuit for wireless communication with a wireless communication unit 72 of the diagnostic apparatus body 42 to be described later is mounted.

In the probe of the invention, the number of integrated circuit boards is not limited to two but may be one. Alternatively, three or more integrated circuit boards may be used, as exemplified by the case where another board is used as the integrated circuit board for controlling the probe 10.

In the probe 10 of the invention, the case 12 has a concave shape to set the grip portion 12G for an operator to hold the probe 10. The battery 16 is disposed within the case 12 at the position corresponding to the grip portion 12G.

The probe 10 of the invention having such a configuration ensures the safety of an operator manipulating the probe 10 from heat upon the diagnosis using an ultrasound diagnostic apparatus.

To be more specific, during its use (during the diagnosis), the probe 10 generates heat not only from the ultrasonic wave unit 14 but also from the battery 16, the control board 18 and the communication board 20. The amount of heat generation or heat release from the control board 18 and the communication board 20 each serving as the integrated circuit board is large but the amount of heat generation from the battery 16 is not so large.

Therefore, the probe 10 of the invention which includes the battery 16 disposed inside the case 12 at the position corresponding to the grip portion 12G set in the case 12 can ensure the safety of an operator from heat by suppressing the increase in the temperature of the grip portion 12G held by the operator.

In the illustrated embodiment, the grip portion 12G is set on the rear side of the ultrasonic wave unit 14 with respect to the direction of transmission of ultrasonic waves (the direction indicated by arrow "a" in FIGS. 1A and 1B) and the battery 16 is disposed between the ultrasonic wave unit 14 and the functional units other than the ultrasonic wave unit 14 (i.e., the control board 18 and the communication board 20).

Having such a configuration, the ultrasound probe can suppress direct heat transfer from the control board 18 and the communication board 20 (functional units other than the battery 16) at elevated temperatures to the ultrasonic wave unit 14. As a result, heat generation in the ultrasonic wave unit 14 can be suppressed while improving the stability thereof.

In the probe 10 of the invention, the grip portion 12G being used preferably has a temperature which is equal to or lower than the human body temperature, that is, equal to or lower than 37° C. More specifically, it is preferred to set the shape of the case 12, the positions of the respective functional units, and the placement of thermally conductive members and a heat insulator 36 to be described later so that the grip portion 12G being used is kept at a temperature of 37° C. or less.

Operators can thus have further improved safety and comfort.

In the probe 10 of the invention, the shape of the grip portion 12G is not limited to the illustrated concave shape.

Various configurations which are used to set the grip portion in known ultrasound probes can be used, as exemplified by continuous formation of grooves, fitting of a cover with anti-slip function, formation of a portion in which a finger can be caught and descriptive setting of the grip portion.

Irrespective of which configuration is selected, the functional units other than the battery 16 are preferably not provided at the position corresponding to the grip portion 12G in the case 12.

In a preferred embodiment, the functional units of the illustrated probe 10 are independently provided with thermally conductive members.

More specifically, the ultrasonic wave unit 14 is provided with two plate-like thermally conductive members 14a so as to sandwich the ultrasonic wave unit 14 therebetween from the lateral sides (in the direction perpendicular to the direction in which the ultrasound transducers 46 are disposed). The battery 16 is provided with two plate-like thermally conductive members 16a so as to sandwich the battery 16 therebetween from the lateral sides. In addition, a plate-like thermally conductive member 18a is placed in contact with the opposite side of the control board 18 from the battery 16 and a plate-like thermally conductive member 20a is placed in contact with the opposite side of the communication board 20 from the battery 16.

The thermally conductive members 14a, 16a and 18a (20a) are shown by broken lines in FIG. 1A in order to clearly show the configuration of the probe 10 or the interior of the case 12.

The thermally conductive members 14a, 16a, 18a and 20a extend from the respective functional units to the rear end of the case 12 in the direction of transmission of ultrasonic waves (direction indicated by arrow "a") and are connected to the radiator fins 26 provided for the individual thermally conductive members.

Therefore, the number of the radiator fins 26 provided in the illustrated probe 10 is six corresponding to the number of the thermally conductive members. The invention is not limited to this and a plurality of thermally conductive members may be connected to one radiator fin 26. Conversely, a plurality of radiator fins may be connected to one thermally conductive member.

In the preferred embodiment, the functional units of the illustrated probe 10 independently include thermally conductive members, which enables heat generated from the individual functional units to be efficiently transferred from the functional units to be released to the outside of the probe 10.

Therefore, operators can have further improved safety from heat in the grip portion 12G.

The thermally conductive members enable heat in the ultrasonic wave unit 14 to be appropriately released to the outside of the unit while appropriately suppressing the heat transfer from the battery 16 and the integrated circuit boards (i.e., the control board 18 and the communication board 20) to the ultrasonic wave unit 14. Therefore, the thermally conductive members can suppress the heating of the ultrasonic wave unit 14 to appropriately ensure the safety of subjects from heat and prevent the ultrasonic wave unit 14 from suffering from power reduction or destabilized operation due to heat while also increasing the power of ultrasonic waves to be transmitted.

These thermally conductive members also enable the effect of heat release from the probe 10 to the outside to be improved. Therefore, limitations to the method of actuating the probe 10 (ultrasonic wave unit 14) due to heat generation are also reduced.

Therefore, limitations to the actuation voltage can be reduced in the actuation method in which, for example as in color Doppler mode, the actuation voltage must be reduced more than in B-mode because of heat generation in the probe. As a result, the effect of improving the sensitivity owing to the improved actuation voltage, for example the improvement of the Doppler sensitivity in color Doppler mode can also be obtained depending on the actuation method used.

The thermally conductive members used in the probe 10 of the invention are not particularly limited and various known thermally conductive members can be used, as exemplified by thermally conductive plates or sheets made of materials with high thermal conductivity such as aluminum and copper.

In particular, a thermally conductive plate or sheet which has a large difference between the thermal conductivity in the planar direction (x-y direction (predetermined two-dimensional direction)) and that in the thickness direction (z direction or direction perpendicular to the two-dimensional direction) and has a high thermal conductivity in the planar direction is advantageously used. Preferred examples of such a thermally conductive member include PGS Graphite Sheet (Panasonic Electronic Devices Co., Ltd.) and other pyrolytic graphite plates or sheets.

The effect obtained by using such thermally conductive members may be equivalent to the mutual insulation of the thermally conductive members as in the case of using the heat insulator 36 to be described later.

As shown in FIGS. 1A and 1B, the thermally conductive member may be simply brought into surface contact with the maximum surface or heat-generating portion of the functional unit so that heat in the functional unit may be transferred to the outside of the unit.

However, when using a thermally conductive member having a higher thermal conductivity in the planar direction than in the thickness direction (for the sake of convenience, this property is hereinafter referred to as "anisotropic" and the property that the thermal conductivity does not vary with the direction as in copper is hereinafter referred to as "isotropic") such as a pyrolytic graphite plate, sufficiently high heat transfer performance may not be obtained by a simple surface contact of the thermally conductive member with the heat-generating portion if the thermal conductivity in the planar direction greatly differs from that in the thickness direction.

In such a case, as is seen from the control board 18 conceptually shown in FIG. 2A, heat in the control board 18 can be transferred to the outside by joining an isotropic thermally conductive sheet 30 made of a material with a large thermal conductivity such as copper to an anisotropic thermally conductive sheet 32 made of a material such as pyrolytic graphite at their ends or end surfaces to form a thermally conductive member 18*a* and disposing the thermally conductive member 18*a* so that the isotropic thermally conductive sheet 30 comes in contact with the heat-generating portions of the integrated circuits (IC) 34.

Figure 2B:
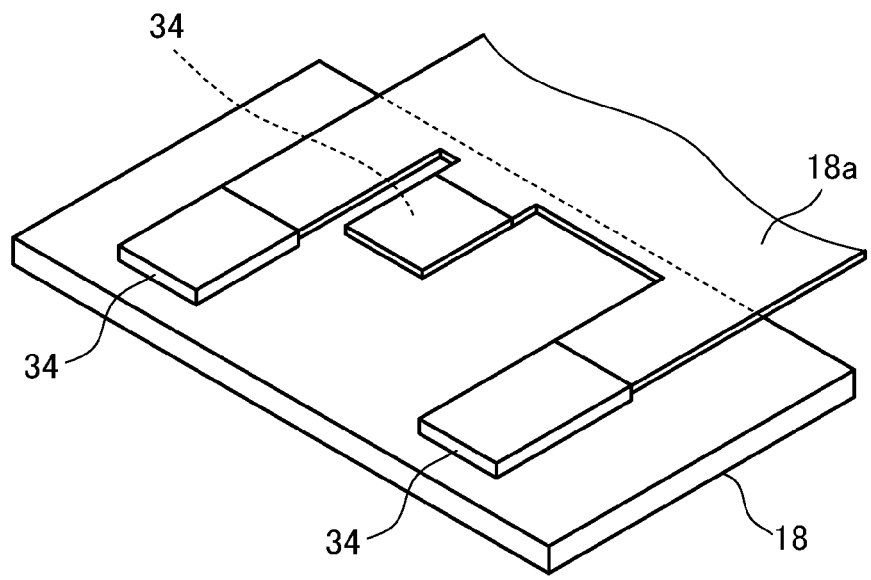

Alternatively, as is seen from the control board 18 conceptually shown in FIG. 2B, heat in the control board 18 may be transferred to the outside by cutting an anisotropic thermally conductive sheet made of a material such as pyrolytic graphite according to the configuration of the control board 18 (functional unit) to obtain a thermally conductive member 18*a* (anisotropic thermally conductive sheet) and disposing the thermally conductive member 18*a* so that the end portions of the thermally conductive member 18*a* come in contact with the heat-generating portions of the integrated circuits 34.

The thermally conductive members are not limited to the case where all the functional units are independently provided with these members.

More specifically, in this invention, it is preferred for at least two functional units preferably including the ultrasonic wave unit 14 to independently include at least one thermally conductive member. In such a case, the other functional units may share a single thermally conductive member or have no thermally conductive member.

However, it is preferred for all the functional units to independently have at least one thermally conductive member as in the illustrated embodiment in terms of improving the safety of subjects and operators from heat, the stability of the operation of the ultrasonic wave unit 14 and the power of ultrasonic waves transmitted from the ultrasonic wave unit 14.

In the probe 10 shown in FIGS. 1A and 1B, the diagonally shaded area in the case 12 is preferably filled with the heat insulator 36. That is, the illustrated probe 10 preferably uses the heat insulator 36 to achieve heat insulation between all the functional units and thermally conductive members.

As with the thermally conductive members, the probe 10 having such a configuration can further improve the safety of operators from heat in the grip portion 12G, appropriately ensure the safety of subjects from heat, and appropriately prevent the power reduction or destabilized operation of the ultrasonic wave-generating unit due to heat.

In the probe 10 of the invention, the heat insulator 36 is not particularly limited and various known heat insulators can be used.

Exemplary heat insulators include urethane insulation and epoxy silicone resin materials containing micro-hollow spheres.

In the probe 10 of the invention, the heat insulator 36 is not limited to the case in which the heat insulator is filled so as to insulate all the functional units and thermally conductive members from each other.

More specifically, the heat insulator 36 may be filled so as to insulate only part or all of the functional units from each other, or insulate only part or all of the thermally conductive members from each other, or insulate only part of the functional units and thermally conductive members from each other.

However, it is preferred to fill the heat insulator 36 so as to insulate at least all the functional units or all the thermally conductive members from each other because it is possible to improve the safety of operators and subjects from heat, to prevent heat transfer from the ultrasonic wave unit 14, to increase the power of ultrasound waves and to stably actuate the ultrasonic wave unit 14. It is particularly preferred for the heat insulator 36 to be filled so as to insulate all the functional units and thermally conductive members from each other as in the illustrated embodiment.

Figure 3:
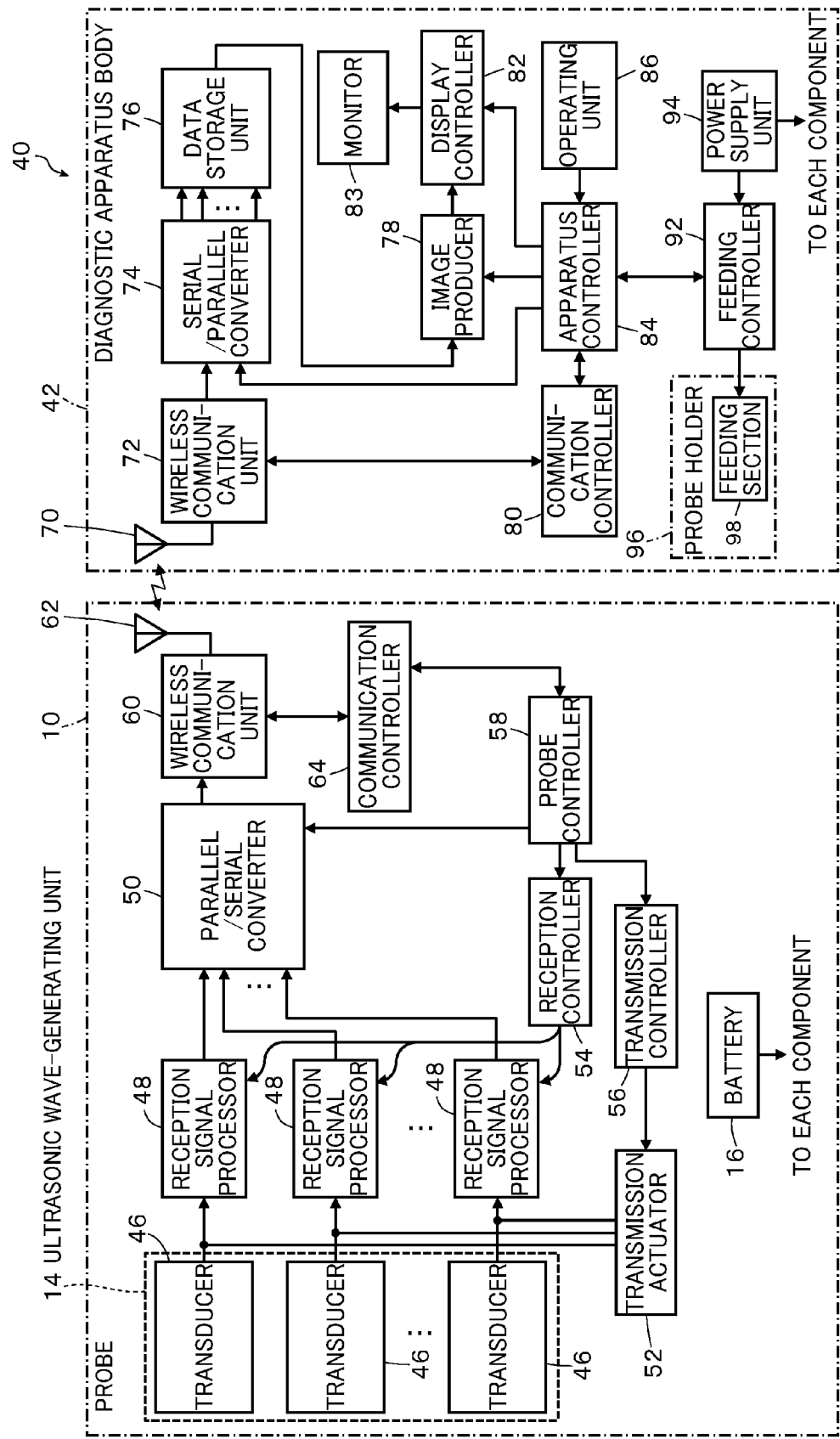
FIG. 3 is a block diagram conceptually showing an ultrasound diagnostic apparatus which uses the ultrasound probe of the invention.

FIG. 3 is a block diagram conceptually showing an embodiment of an ultrasound diagnostic apparatus which uses the ultrasound probe 10 of the invention shown in FIGS. 1A and 1B.

As shown in FIG. 3, an ultrasound diagnostic apparatus 40 includes the probe 10 and the diagnostic apparatus body 42. Ultrasound image data is transmitted from the probe 10 to the diagnostic apparatus body 42 by wireless communication.

As described above, the probe 10 includes the functional units such as the ultrasonic wave unit 14, the battery 16, and the control board 18 and the communication board 20 (not shown in FIG. 3) each serving as the integrated circuit board.

As described above, the ultrasonic wave unit 14 is obtained, for example, by covering a one-dimensional or two-dimensional array of ultrasound transducers 46 (hereinafter referred to as "transducers 46") with an acoustic lens, each of the ultrasound transducers including an ultrasound oscillator, an acoustic matching layer, a backing layer and the like.

Integrated circuits constituting reception signal processors 48, a parallel/serial converter 50, a transmission actuator 52, a reception controller 54, a transmission controller 56 and a probe controller 58 are mounted on the control board 18. On the other hand, integrated circuits constituting a wireless communication unit 60, an antenna 62 for wireless communication and a communication controller 64 are mounted on the communication board 20.

The transducers 46 of the ultrasonic wave unit 14 are individually connected to the corresponding reception signal processors 48, which are connected to the wireless communication unit 60 via the parallel/serial converter 50.

The transducers 46 are also connected to the transmission controller 56 via the transmission actuator 52, the reception signal processors 48 are connected to the reception controller 54 and the wireless communication unit 60 is connected to the communication controller 64. The parallel/serial converter 50, the transmission controller 56, the reception controller 54, and the communication controller 64 are connected to the probe controller 58.

As described above, the battery 16 has no external driving power line but is a power supply for driving the probe 10 wirelessly connected to the diagnostic apparatus body 42 and supplies the components requiring electric power in the probe 10 with electric power.

The battery 16 is recharged if necessary when held in the probe holder 96 of the diagnostic apparatus body 42.

The transducers 46 each transmit ultrasonic waves according to actuation signals supplied from the transmission actuator 52, receive ultrasonic echoes from the subject, convert the received ultrasonic echoes into electric signals and output the reception signals of an ultrasound image to the reception signal processors 48.

The transmission actuator 52 includes, for example, a plurality of pulsers and each transducer 46 (ultrasound oscillator) is supplied with an actuation voltage to oscillate an inorganic piezoelectric device to thereby transmit ultrasonic waves.

The transmission actuator 52 adjusts the delay amounts of actuation signals for the respective transducers 46 based on a transmission delay pattern selected by the transmission controller 56 so that the ultrasonic waves transmitted from the transducers 46 form a broad ultrasonic beam covering an area of a tissue of the subject and supplies the transducers 46 with the adjusted actuation signals.

Under the control of the reception controller 54, the reception signal processors 48 subject the reception signals outputted from the corresponding transducers 46 to quadrature detection or quadrature sampling to generate complex baseband signals, sample the complex baseband signals to generate sample data containing information on the area of the tissue, and supply the parallel/serial converter 50 with the sample data.

The parallel/serial converter 50 converts the parallel sample data generated by the reception signal processors 48 with a plurality of channels into serial sample data.

The wireless communication unit 60 performs carrier modulation according to the serial sample data to generate transmission signals and supplies the antenna 62 with the transmission signals so that the antenna 62 transmits radio waves to achieve transmission of the serial sample data.

The modulation methods that may be employed herein include ASK (Amplitude Shift Keying), PSK (Phase Shift Keying), QPSK (Quadrature Phase Shift Keying), and 16QAM (16 Quadrature Amplitude Modulation).

The wireless communication unit 60 uses the antenna 62 to transmit the sample data to the diagnostic apparatus body 42 through wireless communication with the diagnostic apparatus body 42, receive various control signals from the diagnostic apparatus body 42, and output the received control signals to the communication controller 64.

The communication controller 64 controls the wireless communication unit 60 so that the sample data is transmitted with a transmission wave intensity that is set by the probe controller 58 and outputs various control signals received by the wireless communication unit 60 to the probe controller 58.

The probe controller 58 controls the components of the probe 10 according to various control signals transmitted from the diagnostic apparatus body 42.

On the other hand, the diagnostic apparatus body 42 includes the wireless communication unit 72 to which an antenna 70 is connected. The wireless communication unit 72 is connected to a data storage unit 76 via a serial/parallel converter 74. The data storage unit 76 is connected to an image producer 78. The image producer 78 is connected to a monitor 83 via a display controller 82.

The wireless communication unit 72 is also connected to a communication controller 80; the serial/parallel converter 74, the image producer 78, the display controller 82, and the communication controller 80 are connected to an apparatus controller 84. The apparatus controller 84 is connected to an operating unit 86 for an operator to perform input operations.

The apparatus controller 84 is connected to a power supply unit 94 via a feeding controller 92.

The probe holder 96 for holding the probe 10 which is not in use is further formed in the diagnostic apparatus body 42 and is provided with a feeding section 98.

The wireless communication unit 72 transmits various control signals to the probe 10 through wireless communication with the probe 10. The wireless communication unit 72 demodulates the signals received by the antenna 70 to output serial sample data.

The communication controller 80 controls the wireless communication unit 72 so that various control signals are transmitted with a transmission radio wave intensity that is set by the apparatus controller 84.

The serial/parallel converter 74 converts the serial sample data outputted from the wireless communication unit 72 into parallel sample data. The data storage unit 76 is configured by a memory, a hard disk, or the like and stores at least one frame of sample data converted by the serial/parallel converter 74.

The image producer 78 performs reception focusing on each frame of sample data read out from the data storage unit 76 to generate image signals representing an ultrasound diagnostic image.

The display controller 82 causes the monitor 83 to display an ultrasound diagnostic image according to the image signals generated by the image producer 78.

The monitor 83 includes a display device such as an LCD, for example, and displays an ultrasound diagnostic image under the control of the display controller 82.

The apparatus controller 84 controls the components in the diagnostic apparatus body 42.

The power supply unit 94 supplies the components requiring electric power in the diagnostic apparatus body 42 with electric power.

The feeding controller 92 optionally causes the power supply unit 94 to be connected to the feeding section 98 of the probe holder 96 so that the battery 16 of the probe 10 may be recharged. Then, the feeding section 98 recharges the battery 16 of the probe 10 held in the probe holder 96.

The means for recharging the battery 16 (power supply means) is not particularly limited and various known means may be used, as exemplified by connection between the battery 16 and the feeding section 98 by an electric contact and recharge means using electromagnetic induction.

In the illustrated embodiment, the feeding controller 92 of the diagnostic apparatus body 42 controls the recharge of the battery 16 of the probe 10, for example, as to whether the probe 10 is necessary to recharge or whether the recharge is to be finished. However, the invention is not limited to this and the integrated circuit board provided in the battery 16 may have such a function. The recharge of the battery 16 may be controlled by any known method used in various rechargeable devices.

Not the diagnostic apparatus body 42 but a separately provided, dedicated recharging means may be used to recharge the battery 16 of the probe 10.

In the ultrasound diagnostic apparatus 40, upon the diagnosis, ultrasonic waves are first transmitted from the transducers 46 in accordance with an actuation voltage supplied from the transmission actuator 52 of the probe 10.

The reception signals outputted from the transducers 46 that have received the ultrasonic echoes generated by reflection of the ultrasonic waves on the subject are supplied to the corresponding reception signal processors 48 to generate sample data, which undergoes conversion into serial data in the parallel/serial converter 50 and is then transmitted wirelessly from the wireless communication unit 60 (antenna 62) to the diagnostic apparatus body 42.

In the probe 10 of the invention, the battery 16 having less heat generation is disposed at the position corresponding to the grip portion 12G in the case 12 and therefore operators can make safe diagnoses without being exposed to risk from heat generated in the probe 10.

In the illustrated preferred embodiment, the thermally conductive members are independently disposed in the respective functional units and the probe 10 is filled with the heat insulator 36, and therefore subjects can be prevented from being exposed to risk from heat generated in the probe 10.

The sample data received by the wireless communication unit 72 of the diagnostic apparatus body 42 is converted into parallel data in the serial/parallel converter 74 and stored in the data storage unit 76.

Further, the sample data is read out from the data storage unit 76 frame by frame, and the image producer 78 generates image signals and, based on the image signals, the display controller 82 causes the monitor 83 to display an ultrasound diagnostic image.

While the ultrasound probe of the invention has been described above in detail, the invention is by no means limited to the above embodiments, and various improvements and modifications may be made without departing from the scope and spirit of the invention.

The ultrasound probe can be advantageously employed in an ultrasound diagnostic apparatus used for various diagnoses in the medical settings.

What is claimed is:

1. An ultrasound probe comprising:
   a case having a grip portion set therein;
   functional units disposed in said case, the functional units including at least one ultrasonic wave-generating unit which transmits ultrasonic waves to a subject and receives ultrasonic echoes generated by reflection of the ultrasonic waves on the subject and outputs signals in accordance with the received ultrasonic echoes, and
   a battery disposed in said case at a position corresponding to said grip portion;
   one or more integrated circuit boards configured to perform one or more of performing transmission and reception of ultrasonic waves from and to the ultrasonic wave-generating unit, processing the signals received in the ultrasonic wave-generating unit, and providing wireless communication; and
   three or more thermally conductive members, each of the at least one ultrasonic wave-generating unit, the battery, and the one or more integrated circuit boards having its own exclusive directly connected thermally conductive member of the three or more thermally conductive members extending from the respective functional units and the one or more integrated circuit boards to an end of the case opposite to the ultrasonic wave-generating unit individually and configured to transfer heat generated from one or more of the ultrasonic wave-generating unit, the battery, and the one or more integrated circuit boards to the end of the case opposite to the ultrasonic wave-generating unit individually along independent paths,
   wherein the battery is disposed between the ultrasonic wave-generating unit and the one or more integrated circuit boards, the one or more integrated circuit boards being disposed at a position more distant from the ultrasonic wave-generating unit than the battery.

2. The ultrasound probe according to claim 1, wherein at least one of said functional units is insulated from one or more of other ones of the functional units and the one or more integrated circuit boards.

3. The ultrasound probe according to claim 1, wherein said thermally conductive members are insulated from each other.

4. The ultrasound probe according to claim 1, wherein said thermally conductive members have thermal conductivity which differs between a predetermined two-dimensional direction and a direction perpendicular to the two-dimensional direction, and the thermal conductivity is higher in the predetermined two-dimensional direction than in the direction perpendicular to the two-dimensional direction.

5. The ultrasound probe according to claim 1, wherein one of said at least one integrated circuit board has a function of performing wireless communication with a diagnostic apparatus body constituting an ultrasound diagnostic apparatus.

6. The ultrasound probe according to claim 1, wherein each of the thermally conductive members comprises: a first thermally conductive part which contacts the functional unit or the one or more integrated circuit boards and has isotropic thermal conductivity, and
   a second thermally conductive part which contacts the first thermally conductive part and has thermal conductivity which differs between a predetermined two-dimensional direction and a direction perpendicular to the two-dimensional direction, the thermal conductivity being higher in the predetermined two-dimensional direction than in the direction perpendicular to the two-dimensional direction.

7. The ultrasound probe according to claim 1, wherein the ultrasonic wave-generating unit is disposed closer to an end of the case than the battery and the one or more integrated circuit boards.

* * * * *